(12) United States Patent
Smith

(10) Patent No.: US 6,661,897 B2
(45) Date of Patent: Dec. 9, 2003

(54) TRANSDUCER FOR SENSING BODY SOUNDS

(76) Inventor: Clive Smith, 6571 S. Pontiac Ct., Englewood, CO (US) 80111

( * ) Notice: Subject to any disclaimer, the term of this patent is extended or adjusted under 35 U.S.C. 154(b) by 0 days.

(21) Appl. No.: 10/328,768

(22) Filed: Dec. 23, 2002

(65) Prior Publication Data

US 2003/0128847 A1 Jul. 10, 2003

Related U.S. Application Data

(63) Continuation-in-part of application No. 09/431,717, filed on Oct. 28, 1999, now Pat. No. 6,498,854.

(51) Int. Cl.[7] .............................. A61B 7/14; A61B 5/08; A61B 5/02
(52) U.S. Cl. .......................... 381/67; 600/528; 600/529
(58) Field of Search ............................ 381/67; 600/528, 600/529

(56) References Cited

U.S. PATENT DOCUMENTS

| | | | |
|---|---|---|---|
| 4,072,822 A | * | 2/1978 | Yamada .................... 381/67 |
| 4,582,961 A | | 4/1986 | Frederiksen |
| 4,784,154 A | | 11/1988 | Shirley et al. |
| 4,986,276 A | | 1/1991 | Wright |
| 5,006,952 A | | 4/1991 | Thomas |
| 5,022,405 A | | 6/1991 | Hök et al. |
| 5,932,849 A | | 8/1999 | Dieken |
| 6,002,777 A | | 12/1999 | Grasfield et al. |
| 6,498,854 B1 | * | 12/2002 | Smith ....................... 381/67 |

FOREIGN PATENT DOCUMENTS

JP        10-258053 A   *  9/1998   ............ A61B/8/00

* cited by examiner

Primary Examiner—Forester W. Isen
Assistant Examiner—Laura A. Grier
(74) Attorney, Agent, or Firm—Colin P. Abrahams

(57) ABSTRACT

An acoustic-to-electrical transducer for sensing body sounds is provided. The transducer comprises a diaphragm that can be placed in direct contact with a body, whereby the diaphragm motion directly affects an electromagnetic sensing signal, which is then converted to an electrical signal representation of the diaphragm motion. Such sensing means allows the diaphragm to move freely without mechanical coupling to a secondary transducer, while providing a direct and efficient acoustic to electrical conversion means. The transducer further provides a means for using static diaphragm pressure to control gain and frequency characteristics of the electrical signal. The sensor, circuitry, manufacturing methods and improvements are provided.

25 Claims, 11 Drawing Sheets

TRANSDUCER FOR SENSING BODY SOUNDS

CROSS-REFERENCE TO RELATED APPLICATIONS

This application is a continuation in part application of U.S. patent application Ser. No. 09/431,717 filed Oct. 28, 1999 now U.S. Pat. No. 6,498,854, which is incorporated herein by reference in its entirety.

FIELD OF THE INVENTION

The present invention relates to sensing body sounds, and more specifically, to acoustic-to-electrical transducers used for sensing body sounds, especially in stethoscopes.

BACKGROUND OF THE INVENTION

Stethoscopes are widely used by health professionals to aid in the detection of body sounds. The procedures for listening to and analyzing body sounds, called auscultation, is often difficult to learn due to the typically low sound volume produced by an acoustic stethoscope. Electronic stethoscopes have been developed which amplify the faint sounds from the body. However, such devices suffer from distortion and ambient noise pickup. The distortion and noise are largely due to the performance of the acoustic-to-electrical transducers, which differ in operation from the mechanical diaphragms used in acoustic stethoscopes.

Acoustic stethoscopes have been the reference by which stethoscope sound quality has been measured. Acoustic stethoscopes convert the movement of the stethoscope diaphragm into air pressure, which is directly transferred via tubing to the listener's ears. The listener therefore hears the direct vibration of the diaphragm via air tubes.

Existing electrical stethoscope transducers are typically one of three types: (1) microphones mounted behind the stethoscope diaphragm, or (2) piezoelectric sensors mounted on, or physically connected to, the diaphragm, or (3) other sensors which operate on the basis of electro-mechanical sensing of vibration via a sensing mechanism in mechanical contact with the diaphragm placed against the body Microphones mounted behind the stethoscope diaphragm pick up the sound pressure created by the stethoscope diaphragm, and convert it to electrical signals. The microphone itself has a diaphragm, and thus the acoustic transmission path comprises stethoscope diaphragm, air inside the stethoscope housing, and finally microphone diaphragm. The existence of two diaphragms, and the intervening air path, result in excess ambient noise pickup by the microphone, as well as inefficient acoustic energy transfer. Various inventions have been disclosed to counteract this fundamentally inferior sensing technique, such as adaptive noise canceling, and various mechanical isolation mountings for the microphone. However, these methods are often just compensations for the fundamental inadequacies of the acoustic-to-electrical transducers.

The piezo-electric sensors operate on a somewhat different principle than merely sensing diaphragm sound pressure. Piezo-electric sensors produce electrical energy by deformation of a crystal substance. In one case, the diaphragm motion deforms a piezoelectric sensor crystal which is mechanically coupled to the stethoscope diaphragm, and an electrical signal results. The problem with this sensor is that the conversion mechanism produces signal distortion compared with sensing the pure motion of the diaphragm. The resulting sound is thus somewhat different in tone, and distorted compared with an acoustic stethoscope.

Other sensors are designed to transfer mechanical movement of the diaphragm, or other surface in contact with the body, via some fluid or physical coupling to an electromechanical sensing element. The problem with such sensors is that they restrict the mechanical movement of the diaphragm by imposing a mechanical load on the diaphragm. Acoustic stethoscopes have diaphragms that are constrained at the edges or circumference, but do not have any constraints within their surface area, other than the inherent elasticity imposed by the diaphragm material itself. Thus placing sensors in contact with the diaphragm restrict its movement and change its acoustic properties and hence the sounds quality capacitive acoustic sensors have been disclosed and are in common use in high performance microphones and hydrophones. A capacitive microphone utilizes the variable capacitance produced by a vibrating capacitive plate to perform acoustic-to-electrical conversion. Dynamic microphones that operate on the principle of a changing magnetic field are well-known. These devices typically operate by having a coil move through a static magnetic field, thereby inducing a current in the coil. Optical microphones have been disclosed, which operate on the principle that a reflected light beam is modified by the movement of a diaphragm.

A capacitive, magnetic or optical microphone placed behind a stethoscope diaphragm would suffer from the same ambient noise and energy transfer problems that occur with any other microphone mounted behind a stethoscope diaphragm. A unique aspect of the present invention is that the stethoscope diaphragm is the only diaphragm in the structure, whereas existing microphone-based solutions comprise a stethoscope diaphragm plus a microphone diaphragm, resulting in the inefficient noise-prone methods described previously.

The present invention provides both direct sensing of the diaphragm movement, with the diaphragm making direct contact with the body, while at the same time avoids any change in acoustic characteristics of the diaphragm compared with that of an acoustic stethoscope, since the sensing means does not mechanically load the diaphragm. This results in efficient energy transfer, and hence reduced noise, with acoustic characteristics that are faithful to that of an acoustic stethoscope diaphragm. The present invention discloses three basic embodiments: (a) A capacitive sensor, (b) a magnetic sensor, and (c) an optical sensor.

SUMMARY OF THE INVENTION

According to one aspect of the invention, there is provided a acoustic-to-electrical transducer for detecting body sounds, the transducer comprising (a) a capacitive to electrical conversion means, or (b) a magnetic to electrical conversion means, or (c) an optical (light) to electrical conversion means.

The capacitive to electrical conversion means comprises: a diaphragm having an electrically conductive surface, the diaphragm being mounted in a housing such that the diaphragm can contact a body for body sound detection; a conductive plate substantially parallel to the diaphragm, mounted within the housing, the conductive plate being positioned behind and spaced from the diaphragm to allow diaphragm motion, the diaphragm and conductive plate being connected in the form of an electrical capacitance to electrical circuitry; and a capacitance-to-electrical signal conversion means to convert capacitance changes to electrical signals.

The magnetic to electrical conversion means comprises a diaphragm that is placed against the body, the diaphragm having magnetic elements such as a permanent magnetic surface or electrically-induced magnetic field due to a wire or printed-circuit coil, so that a magnetic field is set up that is subject to change by motion of the diaphragm. The conversion means additionally comprises a magnetic field sensing means to convert the magnetic field changes to an electrical signal. Thus diaphragm motion affects the magnetic field, the magnetic field changes an electrical signal, and acoustic to electrical conversion is achieved.

The optical to electrical conversion means comprises a diaphragm placed against the body, with a light path that can be modified by motion of the diaphragm. A light source transmits visible or infrared light to the diaphragm. The diaphragm reflects the light, which is then detected by an optical detector, and changes in the reflected light signal due to diaphragm motion are then converted to an electrical signal. Another embodiment of the optical method is transmissive, with the light beam passing through an optical element that moves with the diaphragm, the motion of the optical element causing changes in the light beam received by the optical detector.

The present invention provides an acoustic-to-electrical transducer means for the detection of body sounds, such as for use in a stethoscope. The term "body" in this specification may include living or inanimate bodies. Living bodies may include humans and animals, while inanimate bodies may include, by example only, buildings, machinery, containers, conduits and the like. The sensor detects stethoscope diaphragm movement directly, converting the diaphragm movement to an electrical signal which is a measure of the diaphragm motion. Further amplification or processing of the electrical signal facilitates the production of an amplified sound with characteristics closely resembling the acoustic stethoscope sound, but with increased amplification, while maintaining low distortion. This is a significant improvement over the more indirect diaphragm sound sensing produced by the existing microphonic or piezoelectric methods described above. Since the diaphragm motion is sensed directly, the sensor is less sensitive to outside noise than the other methods described, and the signal is a more accurate measure of the diaphragm movement. In the case of the acoustic stethoscope, diaphragm movement produces the acoustic pressure waves sensed by the listener's ears, and in the case of the present invention, that same diaphragm movement produces the electrical signal in a direct manner, the signal eventually being used to drive an acoustic output transducer such as headphones, to set up the same acoustic pressure waves impinging on the listener's ears.

A fundamental advantage of the present invention is that diaphragm movement is not impeded by the acoustic-to-electrical conversion means, since there is a spacing between the diaphragm and other transducer elements. Therefore, the acoustic characteristics of the diaphragm are maintained, and the sound more closely resembles an acoustic stethoscope sound, which is familiar to the current user base of doctors, nurses and others. This is a unique aspect of this invention, in that other acoustic sensors do not require the amount of diaphragm motion required for a contact-type sensing device such as a stethoscope. Thus while other applications require only tens of microns of spacing, and the diaphragms typically move only a few microns when in use, this invention allows for movement of the diaphragm of more than 0.1 mm. Depending on the stiffness of the diaphragm, pressure against the body can result in 0.1 mm, 0.2 mm, 0.5 mm or even 1 mm of diaphragm displacement due to pressure.

The present invention discloses three sensing methods.

The first embodiment utilizes a capacitive sensing method. Capacitive acoustic sensors have been disclosed and are in common use in high performance microphones and hydrophones. However, the present invention uses the stethoscope diaphragm itself as one plate of the capacitive sensor which touches the body surface directly. This method of direct contact capacitive sensing of body sounds as described, is unique.

The sensor comprises a movable diaphragm with a conductive plane or surface, and a co-planar conductive surface (electrode or plate) placed behind the diaphragm, with a space or electrolyte between the two elements. The diaphragm's conductive surface, in conjunction with the second conductive plate, form a capacitor. Movement of the diaphragm due to motion or sound pressure modulates the distance between the diaphragm and plate, producing a change in capacitance. One unique aspect of the invention lies in the fact that the stethoscope diaphragm forms one plate of the capacitor.

A feature of the invention is that the diaphragm, being the same element that makes contact with the body, is primarily sensitive to sounds emanating from the body, rather than sound transmitted through the air from ambient noise. By making contact with the body, the acoustic impedance of the sensor becomes matched to that of the body, rather than the surrounding air. Therefore, the capacitance change due to diaphragm motion is primarily due to body sounds, rather than overall ambient noise.

While a number of means are available for converting the capacitance variation to an electrical signal, the preferred embodiment performs this conversion by charging the capacitance formed by the diaphragm-plate combination to a high DC voltage, via a high resistance. This produces a somewhat constant charge on the capacitor. Movement of the diaphragm then produces a variation in the capacitance. If the capacitor charge is fixed, and the capacitance varies with time, a small AC variation in capacitance voltage is produced. This is sensed by a high-impedance amplifier, which is designed to detect the AC changes in capacitance voltage while avoiding rapid discharge of the capacitor.

A second method for detecting capacitance change is to employ the same diaphragm-plate capacitance in a high-frequency resonant or oscillation circuit, and detect changes in oscillation frequency produced by changes in the time constant of the capacitive circuit.

A third method of constructing a capacitive sensor, and sensing capacitance variation is via the use of an electret technique. This method requires that one or both of the plates of the capacitor formed by the diaphragm-plate be coated with a permanently charged material, such as an electret material, to create a permanent electric field between the plates. Since the plate, or plates, have a permanent electric field between them, the production of a high DC charge voltage is obviated, and voltage changes can be produced due to movement without the need for a DC charge voltage produced via a circuit.

A fourth method of constructing a capacitive sensor is to build the capacitive elements on a semiconductor substrate. In this case, the diaphragm contacts the body, there is a spacing for diaphragm motion, and the rear capacitive plate comprises the aluminum, copper or polysilicon conductive material as one of the layers of a semiconductor process. The fundamental principle of the invention still applies in that a diaphragm in contact with a body forms a movable capacitive electrode.

Any method of detecting capacitance change and converting such change to an electrical signal is encompassed by this invention. This invention therefore covers all such methods for detecting capacitance changes due to diaphragm motion.

It should be noted that while the preferred embodiment comprises a fixed plate behind the diaphragm, the invention includes methods whereby both plates are flexible and form a capacitance. In such a case, the basic principle applies whereby the capacitance varies due to sound pressure from the body, but the second plate is not necessarily rigid.

In the preferred embodiment, the fixed plate is mounted behind the diaphragm. In order to ensure acoustic isolation from external sounds, the fixed plate should preferably be mounted through a means which acoustically isolates it from the housing, or uses a means intended to prevent the fixed plate from vibrating. This is an important improvement which enhances noise isolation.

A variation of the basic principle of operation is to create two capacitors, by having the conductive diaphragm as described, with a conductive plate behind the diaphragm forming one capacitor, and a third plate behind the second, forming a second capacitor. The diaphragm and second plates are charged, while the third, rear plate is connected to an amplifier circuit. This two-capacitor method operates on essentially the same principle, whereby voltage across a charged capacitor varies in response to distance between plates, one plate being formed by the diaphragm. A further feature of the invention, is the method for constructing and producing the diaphragm. The diaphragm material must be flexible, and conduct electricity, in order to perform as a variable capacitor plate sensitive to sound pressure. This electrically conductive surface is preferably, but not necessarily, electrically insulated from the surface of the diaphragm that touches the body, for both safety and interference-prevention purposes.

A further feature of the preferred embodiment is the capacitive sensing circuitry connected to the diaphragm-plate capacitor. In the preferred embodiment, the circuit comprises two critical elements: (1) a high voltage DC bias generator with very high impedance, and (2) an AC amplifier with very high impedance to sense AC voltage changes without discharging the capacitor.

The invention also includes methods for signal amplitude control, DC charge voltage control to preserve battery power, and construction and manufacture of the capacitive sensor.

The first magnetic sensor embodiment of the invention comprises a diaphragm with permanently magnetized material adhered to or integral to the diaphragm, such that diaphragm movement results in changes in the magnetic field in the space behind the diaphragm. A magnetic field sensor is than placed at a distance from the diaphragm, but sufficiently close to detect changes in magnetic field due to diaphragm motion. The field sensor then converts magnetic field changes to an electrical signal. The diaphragm is housed such that it can be placed in direct contact with the body for body sound detection.

In another magnetic sensor embodiment, the diaphragm can be placed against the body, and has an electrical conductor on the rear side of the diaphragm such as a wire coil or printed circuit attached to the diaphragm or printed onto the diaphragm. A current in the coil sets up a magnetic field, or senses changes in a magnetic field produced by another coil or permanent magnet that is fixed behind the moving diaphragm. The diaphragm coil, or another magnetic field sensing means, converts changes in the magnetic field due to diaphragm motion to an electrical signal. Thus the coil can either produced the magnetic field and another circuit perform field detection, or the field can be produced by a separate magnet or circuit, and the diaphragm coil can perform field detection.

An optical sensor embodiment of the invention comprises a diaphragm which has optical elements, such as a reflective or transmissive plane integral to the diaphragm structure. A light transmitter, such as a laser or visible or infrared emitter is placed behind the diaphragm. A light sensor such as a photodiode or phototransistor is also placed behind the diaphragm such that it can detect the reflected light signal being modified by diaphragm motion. The sensor then converts the changing light signal to an electrical signal.

In one embodiment of the optical diaphragm structure, light from the emitter strikes the rear diaphragm surface. The surface or an underlying layer has a reflective pattern that produces either a pulsating or variable analog reflection signal that is then sensed by the optical detector and converted to an electrical signal.

In a second embodiment of the optical transducer, an optical structure such as a film is placed normal to the diaphragm plane, on the rear side of the diaphragm. The emitter and detector are placed such that the optical structure is within the light path between emitter and detector. The light path might be transmissive or reflective. In either case, diaphragm motion produces motion in the optical structure attached to the diaphragm, and the light signal is modified by mechanical movement of the diaphragm. This light signal is then converted to an electrical signal.

In all of the above embodiments, and others suggested by the invention, the diaphragm is physically separated from the conversion mechanism so that diaphragm movement is unimpeded. At the same time, the sensing means directly detects diaphragm motion in the form of a changing electric field, magnetic field, or optical signal. Thus the advantages of direct diaphragm sensing are achieved without the mechanical resistance of a mechanical sensor compromising acoustic characteristics of the diaphragm.

DETAILED DESCRIPTION OF THE PREFERRED EMBODIMENTS

Figure 1:
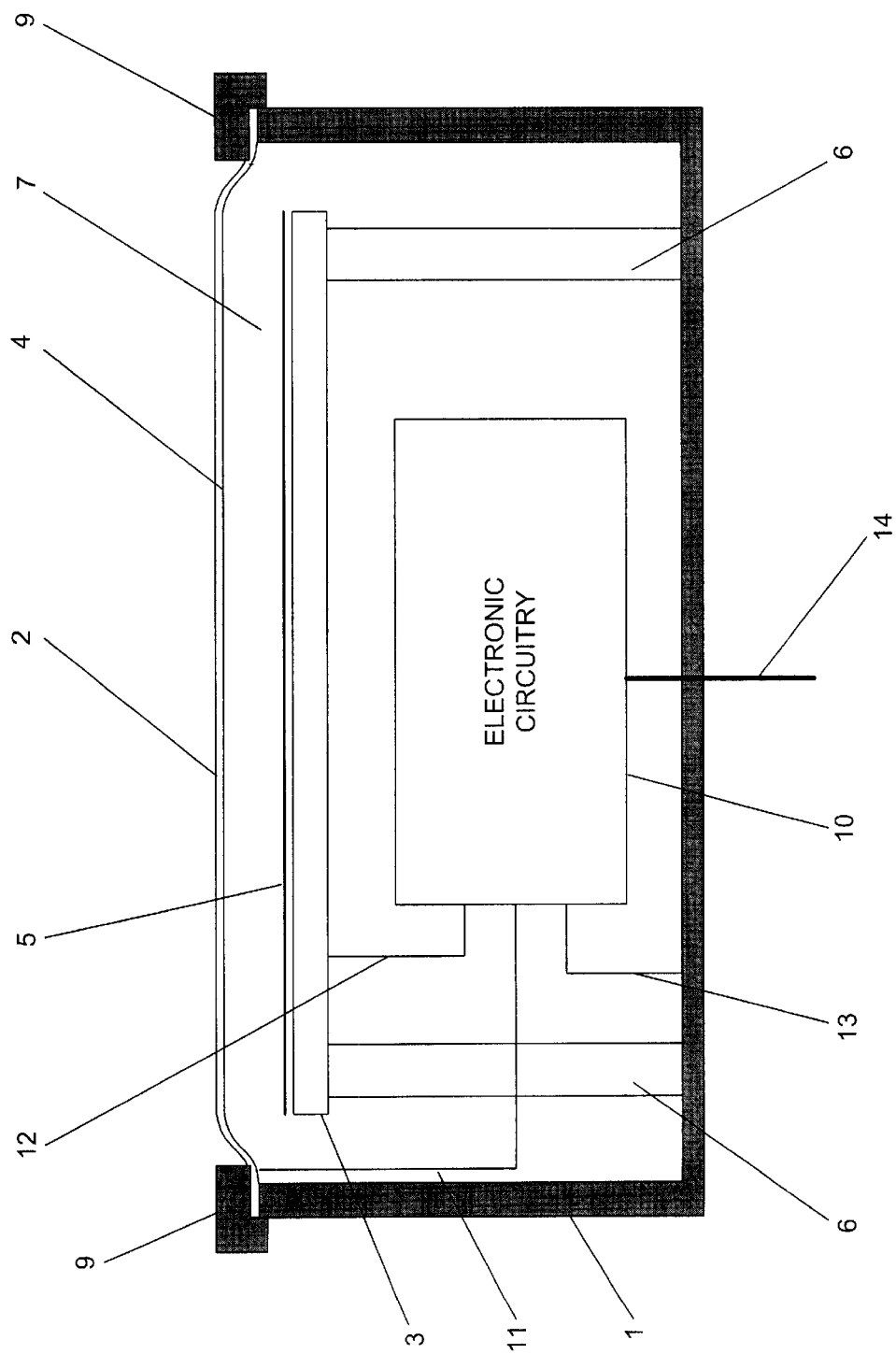
FIG. 1 shows the basic mechanical structure of the invention in one preferred embodiment.

The preferred embodiments are divided into three categories—(a) Capacitive Sensor embodiments, (b) Magnetic Sensor embodiments, and (c) Optical Sensor embodiments. These are all discussed separately below.

A fundamental aspect of the invention, covering all embodiments, is (a) that the diaphragm makes direct contact with the body for sound sensing, (b) the diaphragm is an integral part of the acoustic-to-electric transducer mechanism rather than simply transmitting sound waves via air to a second acoustic-to-electrical transducer i.e. in this invention the diaphragm motion itself is converted to an electrical signal and (c) the mechanical structure of transducer elements other than the diaphragm do not make direct contact with the diaphragm and hence the conversion means does not impede diaphragm motion or place a mechanical load on the diaphragm.

The benefit of this method is that the acoustic properties of the diaphragm are essentially the same as those of an acoustic stethoscope due to the freedom of movement of the diaphragm, and the direct conversion of diaphragm motion that ensures efficient energy conversion from acoustic to electrical energy. Further, the direct conversion method decreases or eliminates the insertion of ambient noise into the conversion process, since ambient noise usually enters the system between the diaphragm and any secondary transducer.

Another unique aspect of the invention is the operation of the diaphragm in this invention compared with diaphragms in conventional microphones. In a conventional microphone, the diaphragm does not make physical contact with any body, the sound being coupled from the source via air, or fluid in the case of a hydrophone. The diaphragm displacement is therefore very limited, typically less than 5 microns displacement. The diaphragms are therefore designed to be displaced a few microns, and the spacing of the diaphragm to other elements behind the diaphragm is typically on the order of tens of microns. In most cases, the goal of conventional microphone design is to minimize such diaphragm spacing in order to optimize performance and sensitivity. It is thus counterintuitive to (a) place a diaphragm directly against the body, (b) allow the diaphragm to withstand the large displacements produced by pressure against a body, and (c) to construct a sensor that increases, rather than decreases, the displacement capability of the diaphragm. Thus in stethoscope applications, the prior art either includes placement of a microphone (with its own diaphragm) behind the stethoscope diaphragm, ensuring that the microphone diaphragm cannot contact the body as well as making the system susceptible to noise, or a mechanical coupling is used that loads the diaphragm thereby limiting its ability to move with any substantial displacement as well as modifying the diaphragm's acoustic characteristics. This invention resolves both problems simultaneously.

In the present invention, the spacing between the diaphragm and any other element of the transducer placed behind the diaphragm typically exceeds 0.1 mm, 0.25 mm, 0.5 mm or 1 mm, subject to the stiffness and radius of the diaphragm, and the mounting means. The present invention addresses stethoscope diaphragms which are typically in excess of 25 mm diameter, although smaller diaphragms are also covered by the invention. If the diaphragm mounting means allows substantial diaphragm displacement, the spacing is increased. If the mounting is more rigid, and the diaphragm material sufficiently stiff to withstand pressure, the spacing can be reduced. In the case of an embodiment that is produced by semiconductor processing means, such that the transducer forms part of a semiconductor integrated circuit, the spacing can be made substantially smaller than 0.1 mm, since the diaphragm diameter is then significantly smaller than a conventional stethoscope diaphragm.

All embodiments of this invention include considerations of spacing and diaphragm displacement, and the numerical values defined above cover all embodiments.

Another aspect of the displacement characteristic of the diaphragm in this invention is the capability to allow static pressure from a body to change the steady-state position of the diaphragm about which vibrations occur due to sound. Thus when the diaphragm is pressed against a body for listening, the diaphragm moves from its unpressured position to a new displacement due to pressure. This is referred to as the static displacement. Then acoustic waves produce smaller dynamic displacement or vibration from sub-sonic (5 Hz–20 Hz) through audio frequency range (20 Hz to 20 KHz). In this case, most sounds of interest do not cover the entire audio range, but are limited to approximately 10 Hz to 2000 Hz). In the present invention, the static and dynamic displacements are used to control the sound characteristics of the transducer in a novel way. The static displacement influences the gain or amplitude of the transducer. The static displacement also affects the frequency response of the transducer. Thus the user can control amplitude and frequency characteristics by applying different static pressures to the diaphragm as it is pressed against the body. The prior art seeks to establish uniform amplitude and frequency characteristics for electronic transducers, so that there is no user-to-user variability. This invention exploits the inherent feedback loop that allows a user to hear the amplitude and frequency characteristics, and adjust pressure on the diaphragm to control for the optimal sound characteristics. While acoustic stethoscopes do provide for modification of sound characteristics with pressure, these effects have not been implemented in electronic stethoscope transducers. Further, the acoustic diaphragms that facilitate this effect do so by modification of the effective diameter of the diaphragm. This invention is novel in that diaphragm displacement is used as the controlling parameter, and the means for effecting this acoustic change have not been achieved with electronic transducers in this application.

This invention includes three primary embodiments of the fundamental inventive steps described above—capacitive, magnetic and optical sensing embodiments.

Capacitive embodiments are presented in FIGS. 1 to 9, Magnetic embodiments are presented in FIGS. 10 to 13, and optical embodiments are presented in FIGS. 14 to 17.

With reference to the drawings, FIG. 1 shows the basic mechanical structure of the invention in its preferred capacitive embodiment. A housing 1 contains a capacitive sensing mechanism comprising a movable flexible diaphragm 2, with electrically conductive surface 4, such surface preferable being on the inner surface, placed co-planar to an electrically conductive plate 3, with some intervening space 7 filled with air or an electrically nonconductive fluid or gaseous substance. The diaphragm 2 and plate 3 form a capacitor. Motion of the diaphragm 2 due to sound pressure varies the distance between diaphragm 2 and plate 3, thereby varying the capacitance of the diaphragm-plate capacitance, since the capacitance is inversely proportional to the distance between the diaphragm 2 and the plate 3. A unique aspect of the invention is that the stethoscope diaphragm 2 forms one plate of a capacitive sensor, whereby the motion of the diaphragm 2 varies capacitance, which then varies other circuit parameters in an electronic circuit, to generate a time-varying electrical signal measuring diaphragm motion. The diaphragm motion is then a measure of the sound being detected, and hence the invention forms an effective body sound sensor.

There are various methods for manufacturing the capacitive diaphragm. One method is to use a substrate of glass epoxy of approximately 0.125 mm to 0.635 mm thickness for the diaphragm 2. The substrate in then coated with a conductive paint via a spray painting process, or a vapor deposition of aluminum or other metal is done. This provides the conductive plane 4. The diaphragm can then be coated with an insulation material, to provide the insulation layer 5. This invention is not limited to these methods for producing capacitive diaphragms. Alternative substrate materials include polycarbonate and mylar, as examples. It is also noted that the substrate materials suggested here are also suitable for use in the magnetic and optical embodiments disclosed in this invention. The diaphragm might also be manufactured with other coatings and layers, such as silkscreened paint with product information or other miscellaneous information, such as model numbers, brand names or advertising. Such layers do not affect the operation of the invention.

In a preferred embodiment, the diaphragm 2 is mounted to the housing 1 via an attachment means 9 which provides acoustic isolation or significant acoustic wave attenuation from the housing 1. This can be achieved by selection of a sound absorbing material for the attachment 9, and/or by shaping the diaphragm 2 such that vibration from the outside circumference of the diaphragm 2 is not coupled to the major surface area thereof. The plate 3 is mounted behind the diaphragm via mounting brackets 6, which provides acoustic isolation or attenuation from the housing in order to reduce ambient noise pickup by preventing the plate 3 from vibrating.

The diaphragm 2 is mechanically housed such that it can be placed in physical contact with a body to sense sound from the body by direct physical contact, rather than via a fluid or air medium as is typical of microphones and hydrophones. This imposes on the diaphragm 2 a preferred property that it be capable of a displacement significantly larger than that typically required for a microphone or hydrophone diaphragm, making space 7 larger than that typical of air microphones or hydrophones. In a preferred embodiment, the distance between diaphragm 2 and plate 3 typically exceeds 0.1 mm. This is a somewhat unique characteristic of this sensing application, resulting in a very low diaphragm-plate capacitance.

The displacement of diaphragm 2 that is facilitated by the spacing between diaphragm 2 and plate 3 takes the form of two displacements—a larger static displacement due to static pressure of the diaphragm against the body, and a smaller dynamic displacement due to acoustic vibration. In both cases, the capacitance is changed, and one can consider these two capacitance changes separately.

The dynamic change due to vibration is small and produces sub-sonic and audio-frequency voltage changes.

The static capacitance change due to static pressure applied to the diaphragm provides a unique aspect of this invention by changing the steady-state capacitance of the transducer in use as a function of this static pressure against the body. This static change causes the gain and the passband frequency of the transducer to change, in response to pressure, since the gain is a function of distance between diaphragm 2 and plate 3, and the passband cutoff frequency is a function of the RC time constant of the input stage of the circuit, where R is the input impedance of the amplifier 54, and C is the capacitance of the transducer. Since C is a function of capacitive spacing which is a function of static pressure, the time constant, and hence the transducer frequency response can be affected by pressure changes against the body.

A unique aspect of this invention is that the user is able to control amplification (gain) and frequency response of the transducer by adjusting the pressure applied to the diaphragm 2. Since the user can hear the sound while the invention is in use, the user becomes part of a feedback loop, in which pressure is adjusted by the user to optimize the sounds quality and amplitude according to the user's needs. This is in contrast to conventional capacitive sensors, in which the distance between plates is tightly controlled, and it is counter-intuitive that variation of static capacitance would be beneficial to the user. In most capacitive sensors, the spacing is also too small to allow for much, if any, static variation, since the goal of such devices is to allow only as much spacing as needed for dynamic changes, such as those due to vibration. It has further been assumed that gain and frequency response should also be tightly controlled parameters not subject to user interaction or control.

An alternative embodiment of the invention allows the spacing between the conductive plates of the transducer capacitance to be filled with a deformable material such as foam, or liquid. These embodiments include the characteristics disclosed above for air-filled capacitive spacing.

In a preferred embodiment of the invention, a high voltage potential is generated between the diaphragm 2 and plate 3. Using such a method, electrical insulation is required of a number of elements in the invention. A high-dielectric insulator 5, made from substances such as Mylar film produced by E.I. Du Pont, or Ultem film manufactured by General Electric, is optionally placed between the diaphragm 2 and plate 3. This reduces electronic noise caused by discharge of the capacitance across the space 7 between the diaphragm 2 and plate 3. While the insulator 5 is not essential to sensor operation, it enhances sound quality. The dielectric insulator 5 can be deposited onto the diaphragm 2, as a coating that covers the conductive plane, or it can be deposited or adhered to the plate 3. Alternatively, it can merely be placed between the diaphragm 2 and plate 3. The plate 3 is mounted via a mounting bracket 6 to the housing 1, such mounting bracket being made of a material which provides high electrical isolation, such as nylon or Teflon This prevents trickle discharge of the plate 3. The preferred electrical insulation requirements stated above are relevant to the embodiment of the invention that requires a high voltage potential between the plate 3 and diaphragm 2. Other embodiments do not necessarily require such high quality electrical insulation, since they might rely on methods of capacitance measurement which does not require a significant DC voltage on the capacitance. An embodiment that is included in this invention comprises a diaphragm 2 that forms a capacitance with a conductive plate 3 that is part of a semiconductor integrated circuit. This plate 3 is formed from aluminum, copper or polysilicon conductive material. In this embodiment, the insulator 5 can comprise an insulation layer typical of semiconductor processes such as silicon dioxide.

The electrical connections are shown in FIG. 1, for one embodiment of the invention. An electronic circuit 10 is preferably mounted within housing 1, with connection 13 to the housing 1, connection 11 to the diaphragm conductive surface 4, and connection 12 to the plate 3. External power and signal connections are provided via connection means 14. The principle of operation of the sensor does not require that the associated circuitry be placed within housing 1. However, best performance is obtained by placing amplifier circuitry close to the sensing capacitance. In the case of a semiconductor implementation of the capacitive sensor, the electronic circuit 10 and connections can be included on one integrated circuit, forming a single structure with capacitive sensor and electrical circuitry. In this embodiment, the diaphragm 2 is still mounted such that it can make direct contact with the body for sensing.

Figure 2:
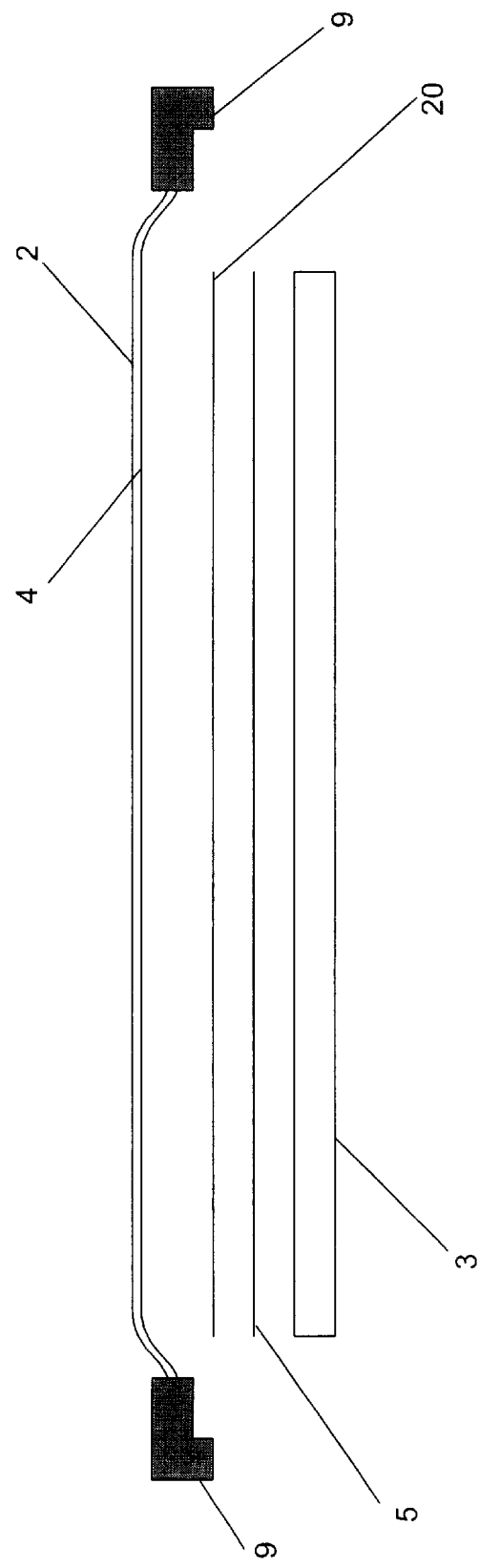
FIG. 2 shows an second embodiment of the sensor capacitive elements of the invention, whereby a double-capacitance is formed.

FIG. 2 shows an alternative embodiment of the sensor capacitive elements of the invention, whereby a double-capacitance is formed. Diaphragm 2 has a conductive surface 4, which forms a capacitance with plate 20, which is comprised of a conductive material. The plate 20 then forms a second capacitance with plate 3, while optional insulation 5 is placed between plate 20 and plate S. The diaphragm 2 is once again mounted to the housing by a mounting clamp 9. The double capacitance method operates on a similar principle of operation to the embodiment of FIG. 1. However, the circuit connections are somewhat different, as described in further detail below.

Figure 3:
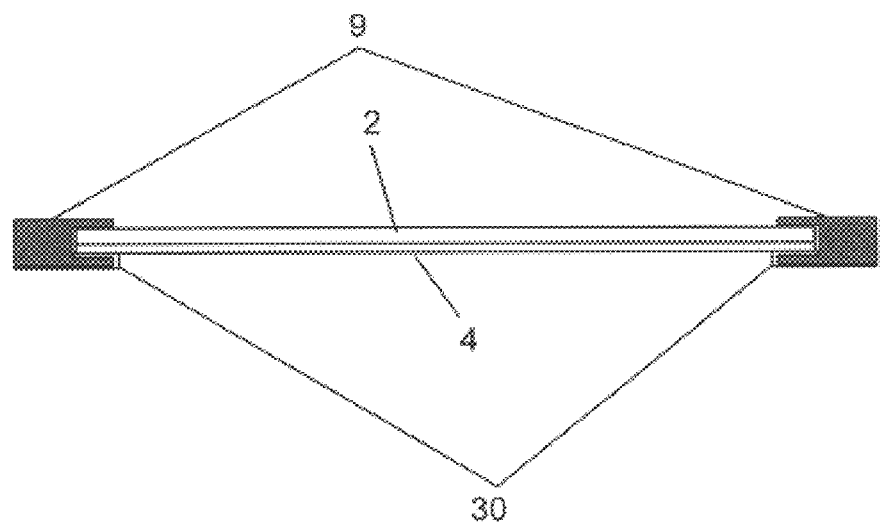
FIG. 3 shows another embodiment of a mounting means for the diaphragm for the capacitive sensor.

FIG. 3 shows an alternative mounting clamp 9 for the diaphragm 2. the mounting clamp 9 is a circular ring shown in cross section. The material from which mounting clamp 9 is made is a sound absorbing substance such as rubber, which prevents vibration from the housing 1 in FIG. 1 from reaching the diaphragm 2 surface. However, the diaphragm has an electrically conductive surface 4 which must be connected to electronic circuitry as indicated in FIG. 1 by connection 11. This connection 11 is achieved, as shown in FIG. 3, by providing a conductive path 30 on the mounting clamp 9. FIG. 3 shows one configuration for achieving acoustic isolation and electrical connection to the conductive surface 4 of the diaphragm 2. If the mounting clamp 9 has a different cross section, or is manufactured from a conductive rubber, the goals of acoustic isolation and electrical connection may still be met.

Figure 4:
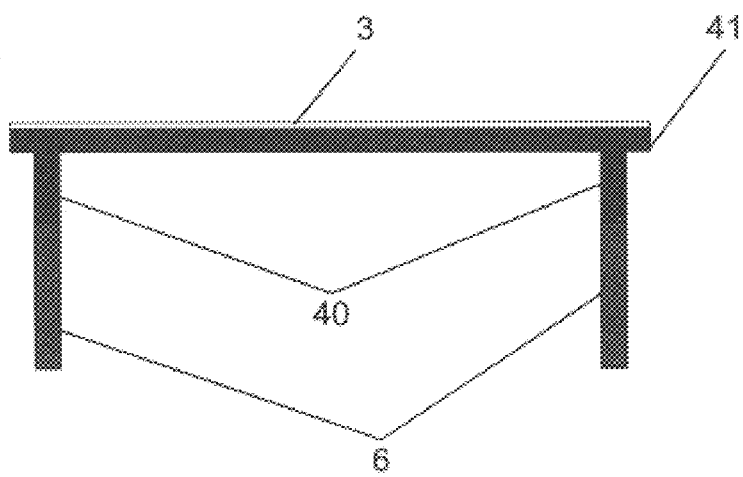
FIG. 4 shows means of ambient sound isolation for the capacitive plate in further detail.
Figure 5:
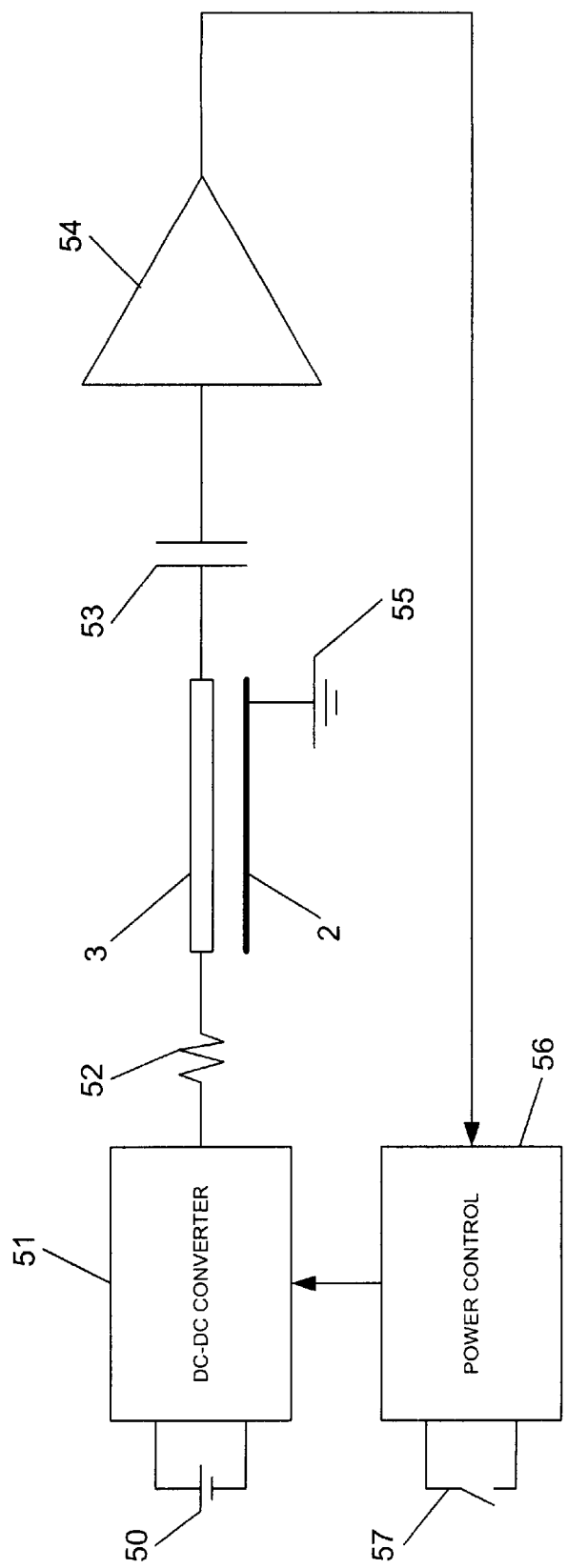
FIG. 5 shows the overall circuit topology of the capacitive sensor when used with a DC-DC charging circuit and associated function.

FIG. 4 shows an important aspect of ambient sound isolation for the plate 3 in more detail. The plate 3 should not vibrate due to housing or external vibrations such as might be produced by ambient noise or handling of the housing 1. The plate 3 must therefore be acoustically isolated from ambient noise sources. This may be achieved by a number of means. A mounting bracket 6 may be constructed with a section 40 which is manufactured from an acoustically absorbent material so that vibrations are attenuated by the section 40. Note that the mounting bracket 6 and the sections 40 are shown as vertical posts. Such mounting may also be achieved by surfaces molded into the housing 1 to support the plate 3, or other means of attachment of the plate 3. The invention simply requires that the plate 3 be acoustically isolated from the housing 1 for optimal performance. FIG. 4 also shows a second alternative to acoustic isolation for the plate 3. The plate 3 may be mounted on an acoustically absorbent material surface 41, such that vibration in the mounting bracket 6 is attenuated by a surface 41. A third method of acoustic isolation is to manufacture the plate 3 from a conductive foam or other electrically conductive, but acoustically absorbent material. The above three methods provide the same function B to acoustically isolate the plate 3. Other methods may be applied to achieve the same goal. An alternative strategy to acoustically isolating plate 3 is to manufacture plate 3 with sufficient mass that acoustic energy does not easily produce vibrations in plate 3. Another alternative methods is to rigidly mount plate 3 to the housing 1, such that the overall plate-housing structure has sufficient mass and rigidity to withstand external acoustic vibration. The method of operation of the preferred embodiment is to develop an electric field in the capacitor formed by the diaphragm 2 and the plate 3 shown in FIG. 1. There are a number of methods for creating this electric field. In a preferred embodiment, a DC source 51, which is a DC-DC boost circuit, is connected to the capacitance via a high-impedance connection 52 as shown in FIG. 5. The DC-DC converter 51 converts low voltage from battery 50 to a high voltage. A voltage of greater than 50V is desired, and significantly higher voltages, on the order of 600v1000V, are feasible in the device. Larger voltages produce larger gain in the mechanical displacement to electrical signal transfer function. The high voltage passed via resistor 52 to the plate 3 results in the plate 3 being at a high voltage potential relative to the diaphragm 2, which is placed at ground reference potential 55 in a preferred embodiment, since this provides electromagnetic shielding as well as functioning as a capacitive plate. An amplifier 54 is connected to the capacitance sensor via a capacitance 53, which isolates the high DC voltage on the plate 3 from the amplifier, while passing time-varying voltage caused by modulation of the diaphragm-plate distance. The input impedance of the amplifier 54 must be significant in order to allow low frequencies to be passed by the capacitor 53.

Circuit functions for the high voltage implementation of the invention are shown in FIG. 5. The plate 3 is charged by the high potential voltage relative to the diaphragm 2 by DC-DC converter 51. Changes is distance between the diaphragm 2 and plate 3 produce a change in the AC, or time-varying voltage across the capacitor, with high resistance 52 and high input impedance of amplifier 54 preventing the capacitor charge from changing too rapidly. The change in the time-varying voltage across the capacitance is amplified by the amplifier 54, to produce a low-impedance time-varying signal which is a measure of capacitance change, and hence diaphragm motion. In certain embodiments, the capacitance of the diaphragm-plate capacitor can be extremely low, on the order of 10 pico-Farads. This results in a very small time constant when the capacitance is connected to external circuitry. An important aspect of the high voltage embodiment of the sensor, is the use of very high-impedance DC charging circuitry, and signal amplification circuitry. In a preferred embodiment, this impedance is preferably above 400 Meg Ohms in both the case of the DC charger and the signal amplifier input, although lower impedances are possible. Thus, in FIG. 5, resistance 52 or the source resistance of DC source 51, and the input impedance of amplifier 54, must all be high impedances.

The housing is preferable placed at ground potential, to act as a shield. Shielding requires that the housing 1 be fabricated from an electrically conductive material, or that a conductive surface by applied to the housing 1. The housing 1 and diaphragm 2 therefore form a shielded cavity for the sensor and electronics. It should be noted that either plate 3 or diaphragm 2 may be placed at a high potential, since it is the charge on the capacitance that is of importance, not the polarity. Note that ground 55 is a relative circuit ground connection, not physically connected to earth ground.

Stethoscopes are typically portable instruments, operated on battery power. A further extension of the invention is in the minimization of power consumption. The DC voltage applied across the diaphragm-plate capacitance in the preferred embodiment is generated from a low-voltage source 50 in a typical battery operated device, as shown in FIG. 5. Since the time constant of the capacitive circuit is, by necessity, sufficiently large to allow frequencies below 100 Hz to be sensed, the DC charge on the sensing capacitance remains at an elevated voltage level for some period of time. Therefore, the DC charge circuit 51 may be operated on a pulsed, or intermittent basis, or indeed shut off, once the DC charge is generated on the capacitor plates. This offers substantial power savings over operating the DC charge circuit continuously, providing the preferred embodiment with substantially longer battery life than a continuously operated DC source would provide. The power control circuit 56 is able to control the high voltage level produced by the DC-DC converter 51 for the purposes of low power operation.

Power control function 56 is operated by either a switch means 57, or automatically by sensing the amplifier 54 output signal. Switch means 57 can also take the form of a control signal from a control microprocessor. In the automatic power control mode, the power control function detects whether the diaphragm is in contact with a body by performing signal processing on the amplifier output signal. There are a number of methods for detecting diaphragm-body contact. One method is to detect a heartbeat waveform. A preferred method is to sense low frequency signal energy in the amplifier output, since this is typically absent when the diaphragm is not in contact with a body.

Since the output signal amplitude from the amplifier 54 is dependent on the DC voltage, the power control function 56 may also be employed to monitor amplifier output and act as an automatic or manual gain control for the sensor, adjusting DC voltage to control amplifier signal output amplitude. This provides the advantage of preserving battery power, as well as providing consistent signal levels. Further, while gain control may be provided at later stages of amplification, there is an advantage to adjusting front end signal level to avoid clipping and to maximize signal-to-noise ratio of the overall amplification process.

Automatic gain control is also optionally implemented in amplifier 54. This is especially important as a means of preventing excessively loud signals from being generated. Amplifier 54 thus optionally includes an automatic muting or attenuation means which is triggered by significant signal levels. These transients typically occur when the diaphragm makes or breaks contact with a body, or when the diaphragm is moved across a body.

Figure 6:
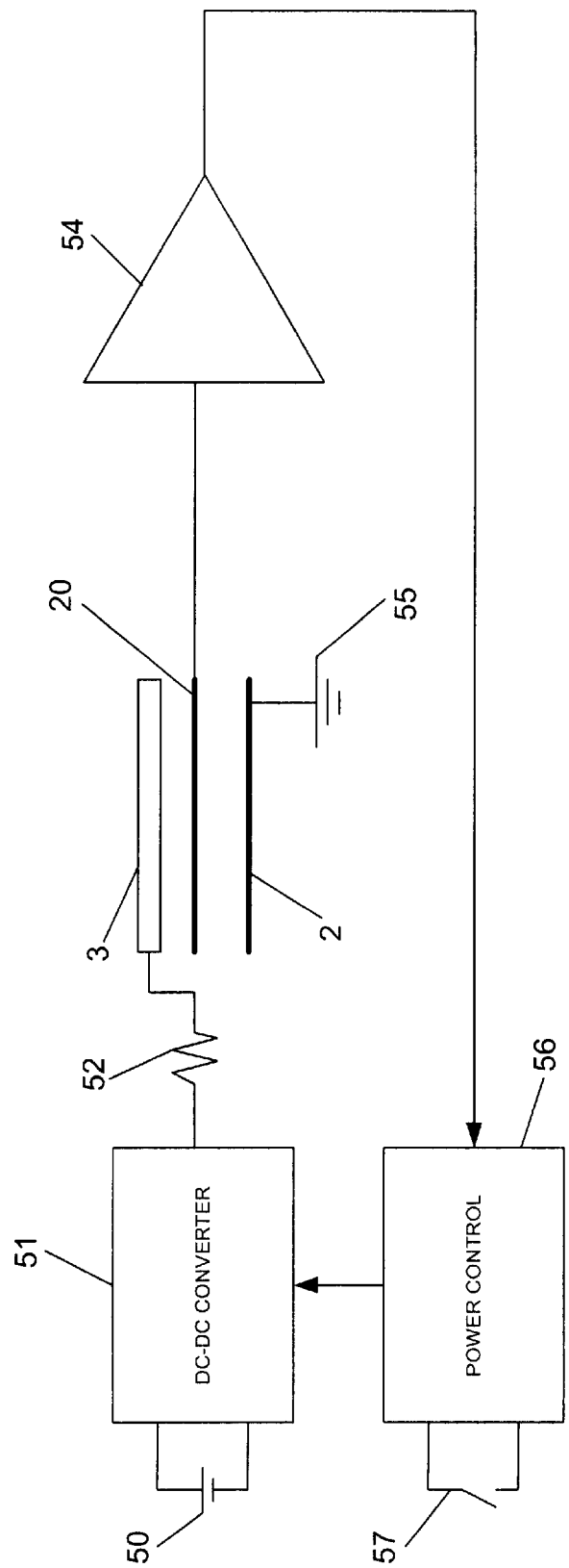
FIG. 6 shows a triple plate capacitance form of the sensor.

An alternative method of creating a capacitive sensor is shown in FIG. 2, with electrical connections shown in FIG. 6. In this implementation, sensor plate 20 is connected to the amplifier input, while plate 3 is at a high voltage as before, and diaphragm 2 is at ground reference potential 55 as before. Circuit operation is as described previously. However, the capacitance formed by plate 20 and the diaphragm 2 serves the dual purpose of sensing and isolating the high DC voltage on plate 3 from reaching the amplifier. It is also possible to exchange plate 20 and plate 3 in FIGS. 2 and 6 to construct a capacitive sensor, and such a structure is electrically equivalent to the circuit shown in FIG. 5.

Figure 8:
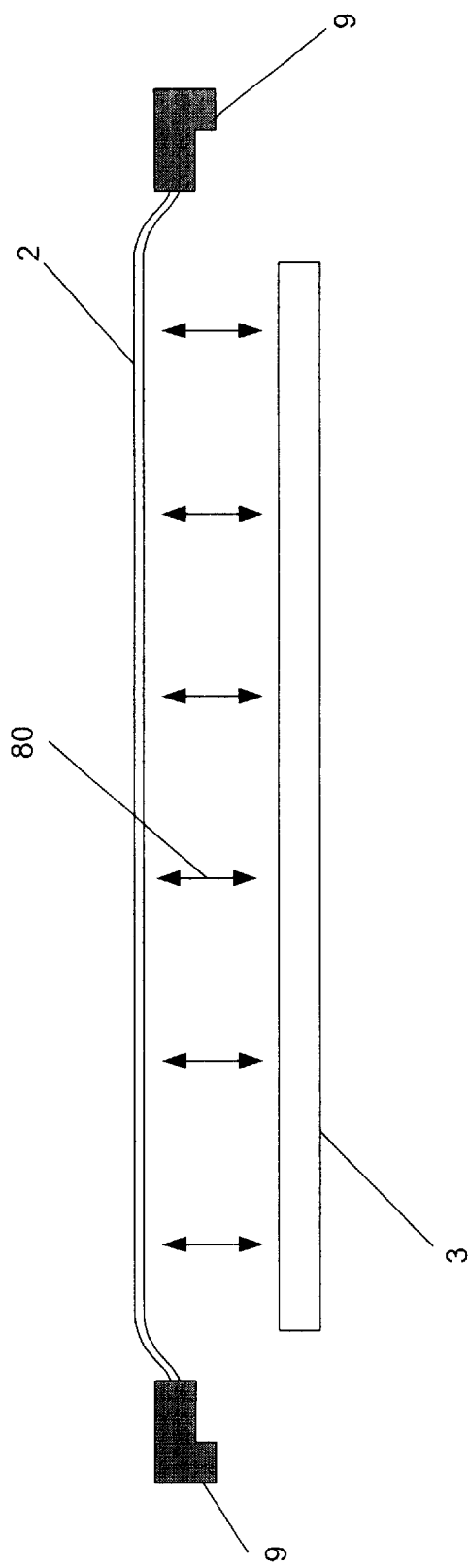
FIG. 8 shows the capacitive sensor wherein the diaphragm, plate, or both are permanently charged such that an electric field exists between the plates obviating the need for a capacitive charging circuit.

An alternative method of establishing a voltage across the diaphragm 2 and plate 3 is shown in FIG. 8 whereby diaphragm 2, plate 3 or both are fabricated with an electret or permanently charged material that maintains a permanent surface charge on one or both elements, setting up an electric field 80 with no external DC drive circuitry. This has the significant advantage that no DC-DC converter is now required, and the time-varying voltage across the diaphragm-plate capacitance may be amplified directly. This method is commonly used in small low cost electret condenser microphones. However, the present invention is unique in that one of the capacitive plates forms a stethoscope diaphragm, allowing physical contact with the body from which sound is to be detected. The manufacture of an electret implementation may be achieved by adhering an electret material to the inside of the diaphragm. Alternatively or additionally, plate 3 may be constructed with an electret surface, or an electret material may be adhered to plate 3. The salient issue is that an electric field must exist between the diaphragm 2 and plate 3, and the invention includes any means by which such a field may be created, either actively using a DC power source, or by using materials which set up a permanent electric field between diaphragm 2 and plate 3. In a semiconductor embodiment, the electret material can be deposited as part of a semiconductor fabrication process. Referring to FIG. 1, it is also potentially advantageous to place a dielectric insulator 5 between diaphragm and plate, even in the electret embodiment shown in FIG. 8. It is also of value in the electret embodiment to facilitate diaphragm motion in excess of 0.1 mm due to static pressure against the body, and also to utilize the change in static capacitance to control or modulate gain and frequency response of the electret transducer. This is not typical of electret microphones in which motion is limited to a few microns, and the capacitive spacing is limited to tens of microns, the intent being that static displacement be limited or tightly controlled. Such diaphragm stiffness would reduce diaphragm sensitivity to acoustic energy. Since a stethoscope diaphragm is typically 25 mm or greater in diameter, significant stiffness would be required to limit diaphragm motion to less than 0.1 mm or greater as defined in this invention. The electret embodiment of this invention is thus unique in that a large diaphragm 2 of at least 25 mm, but potentially as small as 15 mm diameter is spaced from the fixed plate 3 by at least 0.1 mm spacing and the diaphragm 2 is sufficiently flexible to undergo displacements approaching 0.1 mm under pressure from the body during use. It is also unique to exploit such displacement to control gain and bandwidth of the transducer, under influence from a user exerting pressure to control such parameters.

Figure 7:
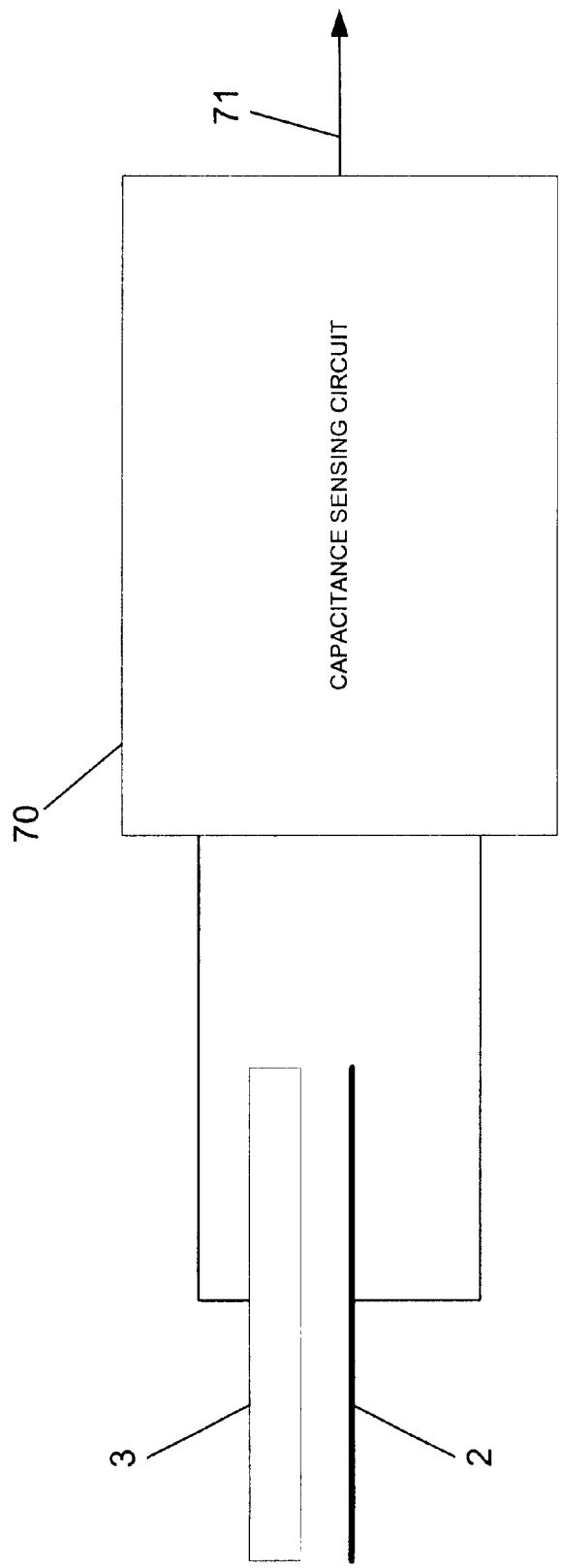
FIG. 7 shows the sensor used in a generalized capacitive sensing circuit.

An alternative method of sensing capacitive change in the sensor is shown in FIG. 7. The plate 3 and diaphragm 2 conductive surfaces are connected to a capacitance sensing circuit 70. The output 71 is an electrical signal, or digital message which transmits the capacitance measurement as a function of time. There are a number of methods of sensing capacitance change due to diaphragm displacement. A few examples are:

a. Connecting the diaphragm-plate capacitance to an oscillator, and converting frequency variation due to capacitance change into a voltage representative of diaphragm motion.
  b. Connecting the capacitance to a resonant circuit and measuring changes in resonant characteristics with changes in capacitance.
  c. Connecting the capacitance to a charging circuit, whereby the charging and/or discharging time of the circuit are converted to a voltage measurement representative of capacitance change.
  d. Connecting the capacitor to a digital measurement and conversion means, whereby capacitance change results in changes in pulse width or digital values.
  e. Connecting the capacitance as a timing element in an analog-to-digital converter circuit whereby digital codes are a function of the capacitance.

All of these methods are based on the fundamental aspect of the invention whereby a capacitance is formed by the diaphragm in conjunction with another element, providing a direct transducer means from diaphragm motion to capacitance change, to electrical measurement. In essence, the above methods use the capacitance as an element in a circuit whose time constant affects electrical waveforms.

The above methods are particularly suited to a semiconductor implementation of the capacitive sensor, since these electronic functions can be implemented very effectively on a semiconductor integrated circuit. Therefore, this invention covers capacitive sensors for body sound detection in which the diaphragm makes direct contact with the body, and the capacitive sensor and associated conversion electronics are combined onto a semiconductor substrate to form an integrated sensor and circuit system.

Figure 9:
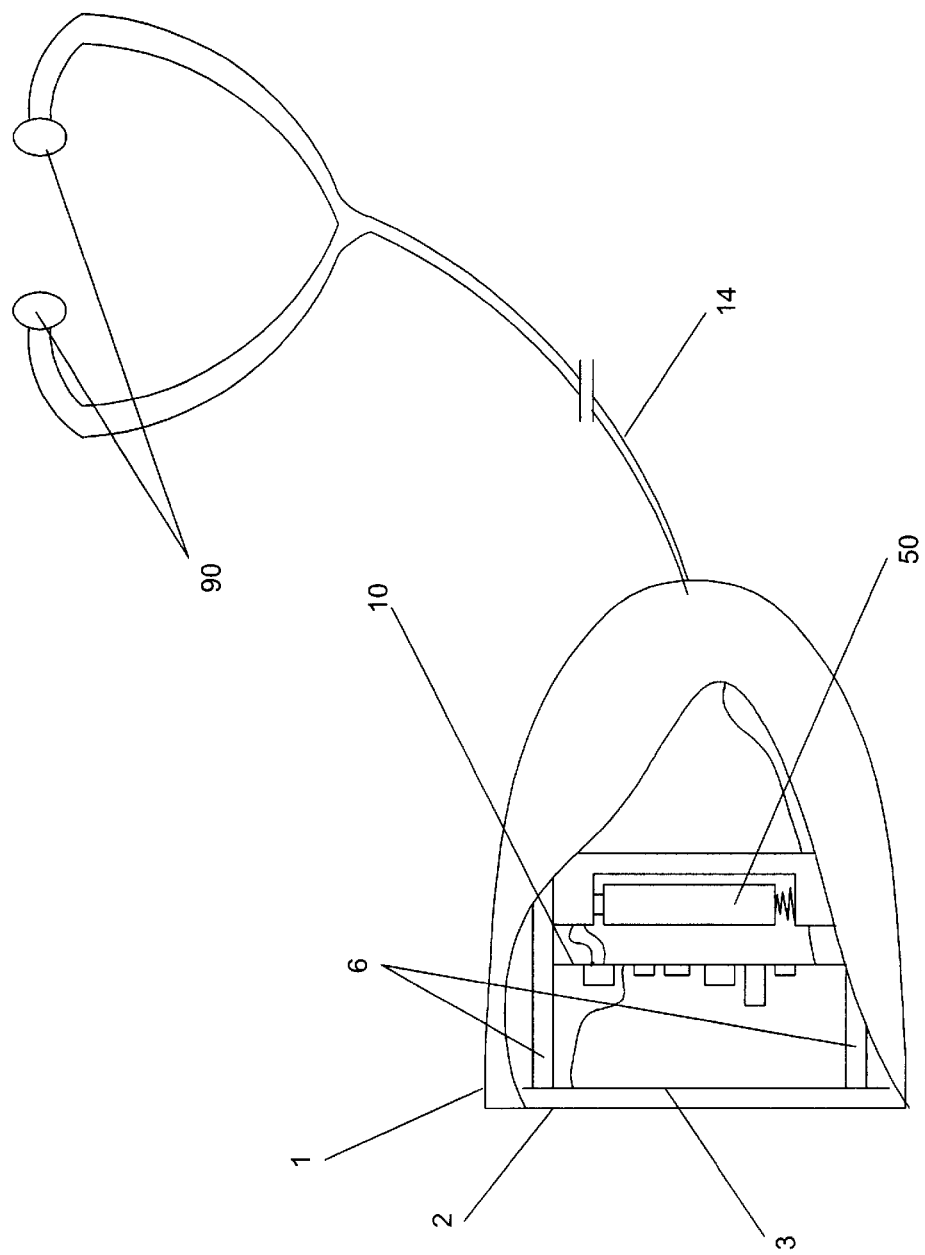
FIG. 9 shows in schematic form and not to scale a stethoscope including the capacitive sensor of the invention.
Figure 10:
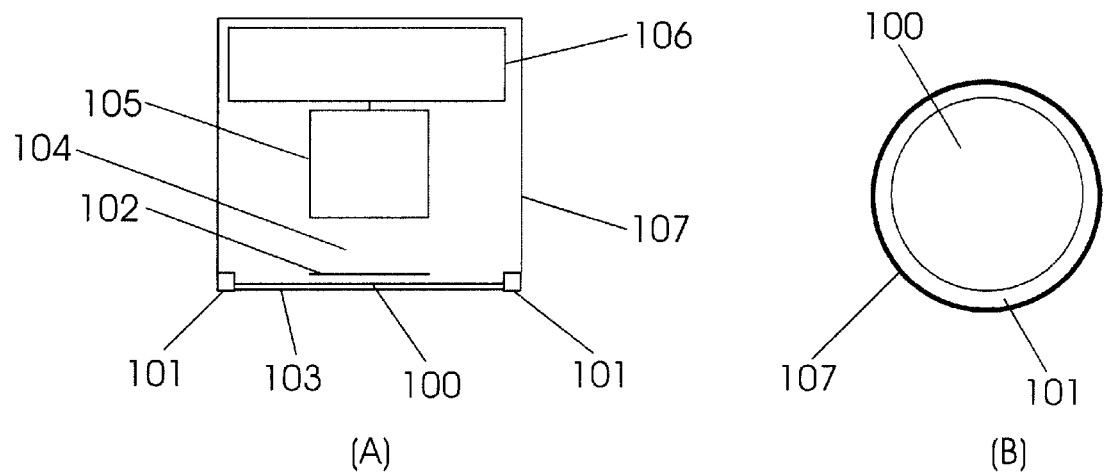
FIG. 10 shows a magnetic sensor embodiment wherein a magnetic material is adhered to or an integral part of a diaphragm.

FIG. 9 shows in schematic form only a stethoscope with the sensor or transducer of the invention. The sensor is much the same as that illustrated in FIG. 1, with the sensor elements shown enlarged in a cutaway view. The housing 1 (shown enlarged and not to scale compared to the remainder of the stethoscope, and partially cut away) houses the elements of the sensor and associated components. The diaphragm 2 is mounted such that it can easily be placed in proximity to a body for sensing sounds. A plate 3 is mounted via a mounting bracket 6 placed behind the diaphragm 2, and parallel to it. Electronic circuit 10 is placed within the housing 1, and powered by a power source 50. An electrical connection 14 transmits audio signals to audio output transducers 90. Further details of the sensor are shown in FIG. 1 and other drawings, and may not be visible in the embodiment as illustrated in FIG. 9.

Note that FIG. 9 illustrates just one embodiment of the invention as used in a stethoscope. Various methods of housing the sensor, placing electronic circuitry within the same or different housing, partitioning electronic circuit functions within the same or different housing, and communicating the signals to the audio transducer are possible without deviating from the fundamental structures and methods disclosed herein. FIG. 9 also shows only a capacitive sensor embodiment of the invention. This invention covers capacitive, magnetic and optical transducer means housed in a stethoscope and figures depicting such transducer embodiments would illustrate the same overall stethoscope structure as that shown in FIG. 9 for the capacitive sensor embodiment.

Stethoscope diaphragms are subject to long term wear and breakage. In a mechanical stethoscope, replacement of the diaphragm is a simple process. In the case of a capacitive diaphragm as described in this invention, it is potentially beneficial to encapsulate the diaphragm 2 and plate 3 in FIG. 1, along with some electronic circuitry 10, in a sealed container that can be easily removed from the main body of the stethoscope. This allows the diaphragm and associated components to be replaced simply, while maintaining a sealed environment for high voltage, fluid, or other elements of the capacitive sensor which exist behind the diaphragm, and which are best kept sealed from atmospheric contaminants, or should not be touched by users. Similarly, the structures shown in FIGS. 10, 11, 12, 13, 14 and 16 for magnetic and optical embodiments can be housed in separable housings that can be attached or detached from a stethoscope or other instrument. The invention thus allows for such elements of the invention to be housed in such a sealed housing, for convenient replacement or repair.

The sensor, enclosed in housing 1 or housing 107 can be used as a peripheral audio sensing device, which can be connected to an external audio recording, transmission or amplifying and reproduction means. Alternatively, housing 1, or a housing 107 is physically attached to a stethoscope, and forms part of the overall stethoscope housing.

While the preferred capacitive embodiment is in the form of a capacitive sensor with a moving diaphragm and fixed plate, it is feasible to form a capacitor with both electrodes being flexible. Such a design includes a diaphragm capacitance formed by two flexible surfaces separated by a dielectric that allows modulation of the distance between the two electrodes due to motion of the two-plate diaphragm. The invention is thus intended to cover any method that comprises a diaphragm acting as part of a capacitive sensor.

FIGS. 10, 11, 12 and 13 show magnetic transducer embodiments of the invention. While the capacitive transducer invention discloses a diaphragm that modulates an electric field, the magnetic diaphragm modulates a magnetic field, operating as follows.

Referring to FIG. 10(A), diaphragm 100 comprises a substrate, and a magnetic material 102, such as a ferroelectric layer. This magnetic material 102 is shown schematically as separate from the diaphragm substrate, however it is to be considered mechanically attached to the diaphragm. A magnetic sensing element 105 such as a Hall element sensor or sensing coil is placed behind the diaphragm, and spaced from it via space 104 which is at least 0.1 mm from any diaphragm elements, the spacing being sufficient to ensure a spacing always exists even during normal use when the diaphragm is placed against the body. The magnetic sensing element 105 detects changes in diaphragm displacement by converting magnetic field changes in spacing 104 to electrical signal changes. The electronic circuit 106 is connected to the magnetic sensing element 105, to convert the raw electrical sense signal to a signal-conditioned output. The magnetic sensing elements, and optionally the electronics, are placed within housing 107 to provide magnetic and electric shielding against external interference. The diaphragm optionally includes magnetic shielding 103.

Referring to FIG. 10(B), diaphragm 100 is mounted within housing 107 via a circumferential mounting means 101 which allows freedom of movement for the center of the diaphragm. Since spacing 104 in FIG. 10(A) allows for unimpeded motion of the center of diaphragm 100, the diaphragm 100 is able to move in the same way as that of an acoustic stethoscope, thereby maintaining acoustic characteristics of an acoustic stethoscope diaphragm. Diaphragm 100 is mounted so that it can directly contact the body for body sound sensing. Diaphragm 100 directly influences the magnetic field in space 104 since the magnetic material 102 is integral to, or mounted onto, diaphragm 100.

The displacement of diaphragm 100 comprises a static displacement and a dynamic displacement. The static displacement affects the gain and frequency characteristics of the signal output by electronic circuit 106, providing the user with control over signal characteristics through application of variable pressure on the diaphragm.

Figure 11:
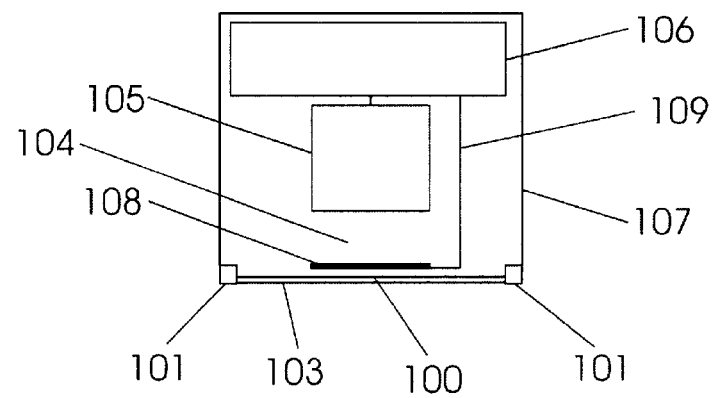
FIG. 11 shows a magnetic sensor embodiment wherein the diaphragm has a coil or printed circuit coil as part of the diaphragm and magnetic assembly.

An alternative to the magnetic embodiment is shown in FIG. 11, and comprises a diaphragm 100 with an electrically-conductive material 108 adhered to or deposited onto diaphragm 100. The conductive material is connected via connection 109 to an electrical circuit 106 such that a magnetic field is produced behind the diaphragm in spacing 104, and changes in magnetic field due to diaphragm motion can be converted to electrical signals by circuit 106. The conductive material 108 in this case might be a conductor which acts like a coil, such conductive pattern being printed, etched or adhered onto the diaphragm. A unique aspect of this magnetic embodiment is that the diaphragm 100 is free to move mechanically due to spacing 104 and mounting means as shown in FIG. 10(B), and the transducing means does not impede diaphragm motion. Further, the mechanical housing 107 allows for the diaphragm to contact the body directly for sensing body sounds, without any intervening air layer between the diaphragm 100 and vibrating surface of the body. Magnetic shielding 103 is optionally included on the diaphragm, so that magnetic fields inside the sensor housing 107 are shielded from interference from external magnetic or electric fields. Such shielding 103 includes materials such as mu-metals, or electrically conductive materials.

The embodiment shown in FIG. 11 can operate in one of two ways. In the first case, discussed above, the conductor 108 creates a magnetic field that is sensed by sensor 105. In the second case, the conductor 108 senses the changes, and element 105 creates the magnetic field rather than sensing it. In either case, a magnetic field exists in spacing 104, and the elements 105 and 108 act in concert to set up the field and sense changes in it due to diaphragm motion.

Figure 12:
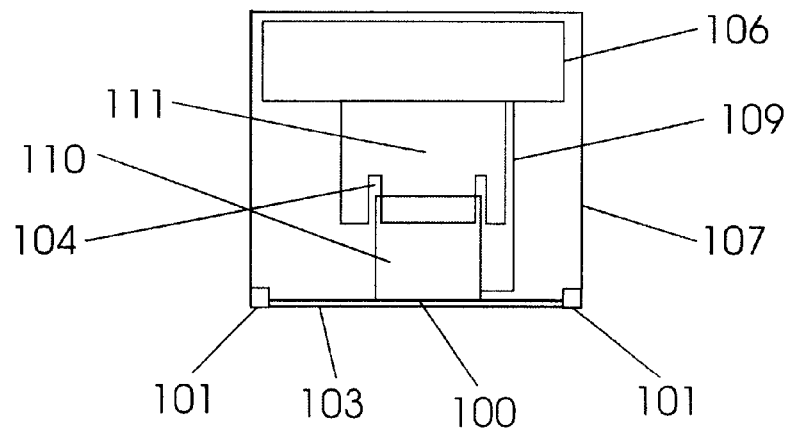
FIG. 12 shows a magnetic sensor embodiment wherein a coil is mounted normal to the diaphragm and a permanent magnet is placed behind the diaphragm to form a dynamic microphone structure.

FIG. 12 shows another magnetic embodiment, in which a coil 110 is mounted normal to the rear side of diaphragm 100. A permanent magnet 111 is mounted such that the magnetic field in coil 110 changes when diaphragm 100 moves due to vibration. Coil 110 is connected via connection 109 to an electronic circuit 106 which produces an electrical signal based on magnetic field changes due to motion of diaphragm 100. Diaphragm 100 is mounted as described above, to provide contact with the body and unimpeded motion, since spacing 104 is greater than 0.1 mm and provides sufficient spacing to ensure that some spacing exists during use.

Figure 13:
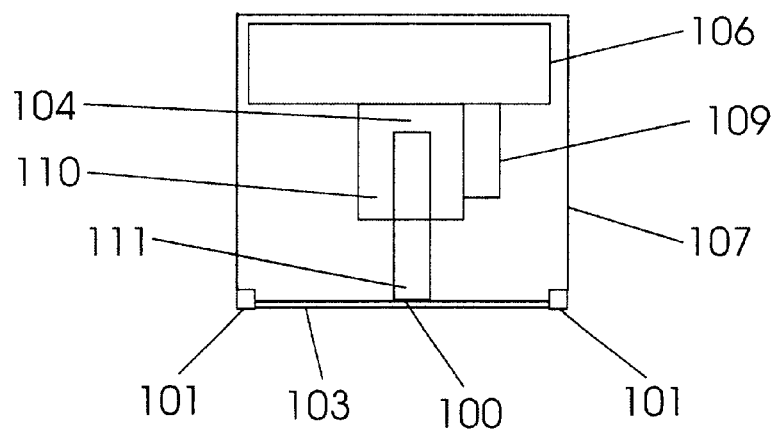
FIG. 13 shows a magnetic sensor embodiment wherein a magnet is mounted normal to the diaphragm with a stationary coil used to sense diaphragm motion.

FIG. 13 shows an embodiment which is functionally analogous to that shown in FIG. 12, except that structurally the coil and magnet are reversed such that coil 110 is fixed, and magnet 111 is mounted to diaphragm 100 and moves with the diaphragm. In other respects, the embodiment in FIG. 13 is as described above for FIG. 12.

In FIGS. 12 and 13, the mounting of the coil or magnet normal to the diaphragm might optionally require a stabilizing member attached to the housing or other mechanical element to hold the normal magnet or coil in place. This invention covers such modifications, since the fundamental magnetic field modulation method is still applicable to such embodiments.

Figure 14:
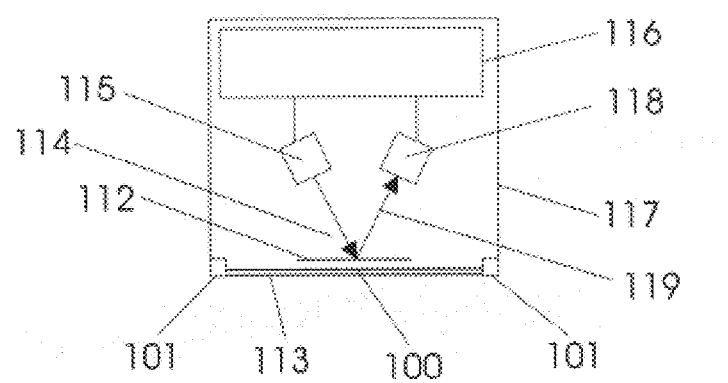
FIG. 14 shows an optical sensor embodiment wherein a light beam is reflected from the back of the diaphragm, and changes reflected light are converted to an electrical signal.

An embodiment which uses optical diaphragm motion detection is shown in FIG. 14. In this embodiment, the diaphragm 100 includes a reflective means 112, such as a layer of optically-reflective material with a pattern which affects reflectance. The reflectance means 112 might be adhered to the diaphragm substrate or printed or etched onto the substrate. In this embodiment, light source 115 emits a visible or infrared or laser light beam 119 which strikes reflectance means 112 and is reflected to light sensor 118, the beam 119 being modified due to motion of diaphragm 100. These optical elements are located within housing 117. Electronic circuit 116 provides drive and sensing signals for emitter 115 and detector 118. The diaphragm 100 is mounted in housing 117 by circumferential mounting means 101. Spacing 114 provides the light path, and ensures that diaphragm 100 has sufficient spacing for static and dynamic displacement as discussed previously in the case of the capacitive embodiment. The optical elements are housed in housing 117 and diaphragm 100 optionally includes a light and/or electromagnetic shield or protect optical and electrical elements from external interference.

The change in light signal 119 in one embodiment shown in FIG. 14 is an angular or intensity change, and is in proportion to the diaphragm displacement. Angular change in reflection is produced by changes in the point at which reflection occurs due to the change in geometry of the light path 119 caused by diaphragm motion. Detector 118 is thus sensitive to positional or angular changes in reflection. The reflective element 112 could also comprise a reflective mirror or lens structure whereby the light hits the structure, and is refracted or reflected by a mirror or lens which modifies the light path or intensity that is reflected to the detector 118.

Figure 15:
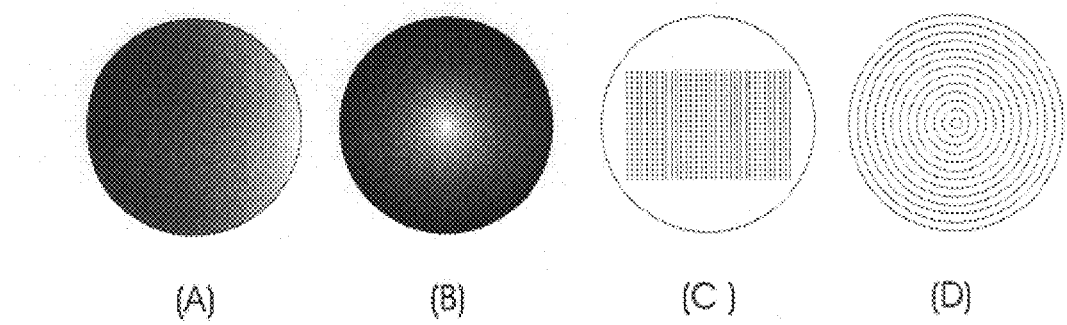
FIG. 15 shows various diaphragm optical reflection patterns that produce changes in the reflected light signal as the diaphragm position changes, and the point of reflection changes.

Intensity change is produced the embodiment in FIG. 14 if diaphragm 10d has a reflective layer 112 that has a variable reflective characteristic that is a spatial function such as those shown in FIG. 15. In this case, as the diaphragm 100 vibrates, the reflection signal 119 changes intensity by being reflected off a location in the pattern that changes with diaphragm displacement.

In FIG. 15(A), the pattern is linear and constantly variable in an analog (continuous) manner, producing an analog signal variation in light signal 119. In FIG. 15(B), this same concept applies, except that the reflectance is a function of diaphragm radius, and the pattern is radial as shown in FIG. 15(B). This has the advantage that the diaphragm can be mounted at any rotational angle in housing 117.

The pattern shown in FIG. 15(C) produces a pulsating variation in light signal 119, as the light beam reflects alternately off a light or dark line. These pulses are then converted to an electrical signal that is a function of diaphragm displacement. FIG. 15(D) operates on the same principle except that the alternating pattern is radial, allowing for diaphragm mounting at any rotational angle in housing 117. The patterns shown are schematic representations, and do not show the resolution that is required to produce high signal-to-noise ratio audio signals that accurately measure diaphragm displacement. The line spacing for the digital modulation schemes shown in FIGS. 15(C) and 15(D) is on the order of more than 10 lines per millimeter, and preferably greater than 50 lines per millimeter.

While some diaphragm spatial reflectance functions are shown in FIG. 15, this invention covers any embodiment in which a diaphragm is placed against the body, and the rear surface of the diaphragm has optical characteristics that allow for a reflected light signal to be modulated by diaphragm motion.

This optical detector embodiment of FIG. 14 is unique in that a diaphragm 100 can contact the body directly due to mounting 101 and housing 107, and the same diaphragm produces changes in the optical signal 119 reflected from the diaphragm and converted to a signal representative of diaphragm motion.

Figure 16:
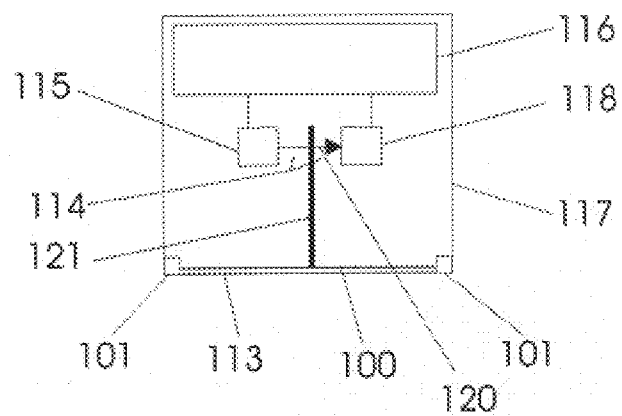
FIG. 16 shows a optical sensor embodiment wherein an optical film or other structure is mounted normal to the diaphragm, such that the structure interferes with a transmitted light source in order to produce an electrical signal that measures diaphragm motion.

In a second optical detection embodiment, shown in FIG. 16, a transmissive method is disclosed, in which the light signal 120 is transmitted from light emitter 115 through a transmissive optical element 121. Spacings 114 in all directions around element 121 ensure that diaphragm motion is unimpeded during use allowing for both static and dynamic displacement of diaphragm 100. Light signal 120 can be visible, infrared and can be a laser light signal. The optical elements are housed in housing 117 and diaphragm 100 optionally includes a light and/or electromagnetic shield or protect optical and electrical elements from external interference.

In FIG. 16, the optical element 121 is mounted to be moved directly by diaphragm 100 motion, and diaphragm 100 can be placed against the body during use, the structure thereby providing very direct signal conversion.

Figure 17:
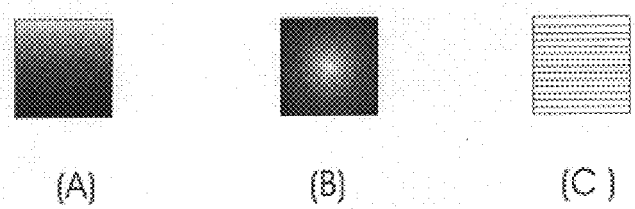
FIG. 17 shows the transmissive light patterns that are applicable to the transmissive reflector shown in FIG. 16.

FIG. 17 shows some embodiments of the transmissive element 121. In FIG. 17(A) a transmission medium is shown that is a linear function of displacement. FIG. 17(B) shows a circular function, and FIG. 17(C) shows a digital pattern which is interrupted by diaphragm motion to produce a pulsating output signal. Transmissive medium- 121 can, in one embodiment, be attached to the housing 117 or other element, in order to ensure that the optical element 121 is mechanically stable. However this attachment does not unduly modify the dynamics of diaphragm 100. This invention covers all transmissive patterns that would result in modulation of light signal 120, not only those shown in FIG. 17. Another transmissive element is a lens structure that modifies the light signal 120 by means of refraction, and this invention includes such methods.

In the case of an optical embodiment, the spacing between any diaphragm elements and other elements can be as low as 0.1 mm but can be of the order of a few millimeters as well. The primary criterion is that the motion of the diaphragm 100 produce sufficient optical beam modulation such that electronic circuit 116 can produce an audio signal that provides a signal-to-noise ratio in excess of 35 db in the audio signal, or produces a signal that can further be processed to produce an audio signal with signal-to-noise ratio in excess of 35 db. This requirement establishes requirements on the resolution of optical elements. Thus the beam width of signal 119 in FIG. 14 or beam 120 in FIG. 16 must be sufficiently narrow to facilitate sufficient signal resolution. The reflectance patterns must also be of sufficient resolution to provide adequate beam modulation. The detection capability is thus a function of beam width, detector sensitivity and noise, reflectance pattern, and beam geometry. It is the final signal integrity that controls these parameters, and hence the requirement must be placed on signal-to-noise ratio, rather than the elements specified separately.

The optical embodiments also have the inherent capability to use static and dynamic displacement to provide gain and frequency control. Since the optical signal can determine actual position or actual displacement from the unpressured null position, circuit 116 can modify gain, frequency response or other signal parameter as a function of steady state or static diaphragm position. Thus the user can, as in the case of capacitive or magnetic embodiments, control signal parameters through static pressure on the diaphragm.

Referring to FIG. 4, which shows the capacitive embodiment of the invention and specifically the mounting of stationary internal elements, wherein the stationary structure is the capacitive plate 3, the magnetic embodiment and optical embodiment have an analogous requirement for their static elements to be resistant to vibration. Thus in FIG. 10 and 11, magnetic element 105 must be held stable, in FIG. 12 magnet 111 must be held stable, in FIG. 13 coil 110 must be held stable, in FIGS. 14 and 16, light emitter 115 and light detector 118 must be held in an immobile stabilized position so that acoustic energy does not produce undesirable motion. In all of these embodiments, the methods shown in FIG. 4, and discussed above apply. Thus a mounting means which either decouples the static elements listed from other vibrating elements such as the housing are required, or the static elements listed must be hald in a stable position by mounting on a mass that is resistant to vibration, or mounted rigidly to the housing so that resistance to vibration is achieved.

In all of the above embodiments, the diaphragm is in contact with the body for vibration detection due to housing construction which allows for such contact, the diaphragm is unimpeded by mechanical to electrical coupling mechanisms in contact with the diaphragm, and the diaphragm motion directly controls an electrical or optical signal. Such direct coupling between acoustic and electrical signaling, while maintaining the mechanical and acoustic characteristics of an acoustic stethoscope diaphragm, are unique aspects of this invention, allowing acoustic stethoscope sound characteristics to be transduced to the electrical domain for further electronic signal processing.

What is claimed is:

1. An acoustic-to-electrical transducer for detecting body sounds, the transducer comprising:

a diaphragm having an electrically conductive surface, the diaphragm being mounted in a housing such that the diaphragm can make contact with the body and vibrate in response to body sounds;

a fixed conductive plate substantially parallel to the diaphragm, mounted within the housing, the conductive plate being positioned at a distance about or exceeding 0.1 mm from the diaphragm, the diaphragm conductive surface and fixed conductive plate forming two plates of a capacitor and connected in the form of an electrical capacitance to electrical circuitry; and a capacitance-to-electrical conversion means to convert diaphragm-plate capacitance changes due to body sound vibration to electrical signals.

2. The transducer according to claim 1, wherein the diaphragm comprises a flexible electrically-insulated substrate with electrically-conductive material deposited or adhered on an inner plane.

3. The transducer according to claim 1, wherein the capacitance is charged to a DC charge voltage by a DC to DC boost circuit, said boost circuit boosting an input DC supply voltage to a significantly higher DC charge voltage.

4. The transducer according to claim 3, wherein the DC to DC boost circuit can be operated intermittently to,reduce battery power consumption.

5. The transducer according to claim 3, wherein the DC to DC boost circuit DC charge voltage magnitude is adjustable as a function of electrical signal amplitude or frequency characteristics of the output signal of the capacitance-to-electrical signal conversion means.

6. The transducer according claim 1, wherein the diaphragm conductive surface is connected to circuit ground potential to provide electromagnetic shielding for the transducer.

7. The transducer according to claim 6, wherein a housing conductive surface is connected to circuit ground potential such that the diaphragm and housing conductive surfaces form an electromagnetically-shielded cavity for electrical circuitry housed within said cavity.

8. The transducer according to claim 1 further comprising means to create a permanent static electric field between the diaphragm and conductive plate.

9. The transducer according to claim 1, wherein the housing which includes the diaphragm and conductive plate forms a removable module which is attachable to or detachable from a stethoscope body, and includes means for mechanically and electrically coupling the module to a stethoscope body.

10. The transducer according to claim 1 wherein the mounting means for the diaphragm and fixed conductive plate include acoustic isolation means to reduce vibrations of the diaphragm or conductive plate due to ambient sound; and electrical connection means to connect diaphragm-plate capacitance to capacitance-to-electrical conversion means.

11. The transducer according to claim 1 wherein the capacitance-to-electrical conversion means includes one of the following steps for converting capacitance changes to electrical signals: (a) Varying the frequency of oscillation of an oscillator as a function of capacitance, (b) Varying the time constant of a circuit as a function of changing capacitance, (c) Generating a digital output signal which is a function of capacitance.

12. The transducer according to claim 1, wherein the space between the diaphragm conductive surface and fixed conductive plate further includes a layer of high dielectric electrical insulation material.

13. An electronic stethoscope including an acoustic-to-electrical transducer for detecting body sounds, the transducer comprising:

a stethoscope diaphragm having an electrically conductive surface, the diaphragm being mounted in a stethoscope chestpiece such that the diaphragm can contact the body for body sound detection and vibrate in response to body sounds;

a fixed conductive plate substantially parallel to the diaphragm, mounted within the chestpiece, the conductive plate being positioned at a distance about or exceeding 0.1 mm from the diaphragm, the diaphragm conductive surface and fixed conductive plate forming two plates of a capacitor and connected in the form of an electrical capacitance to electrical circuitry;

a capacitance-to-electrical signal conversion means to convert diaphragm-plate capacitance changes due to body sound vibrations to electrical signals;

the stethoscope further comprising signal amplification means and at least one electrical-to-acoustic transducer connected to signal amplification means, to reproduce body sounds as detected by said transducer.

14. An acoustic-to-electrical transducer for detecting body sounds, the transducer comprising:

a diaphragm having an electrically conductive surface, the diaphragm being mounted in a housing such that the diaphragm can make contact with the body and vibrate in response to body sounds;

a fixed conductive plate substantially parallel to the diaphragm, mounted within the housing, the conductive plate being positioned behind the diaphragm the conductive plate being positioned at a distance about or exceeding 0.1 mm from the diaphragm, the diaphragm conductive surface and fixed conductive plate forming two plates of a capacitor and connected in the form of an electrical capacitance to electrical circuitry;

a capacitance-to-electrical conversion means to convert diaphragm-plate capacitance changes due to body sound vibration to electrical signals;

the capacitance-to-electrical conversion means having gain and frequency response characteristics that are adjustable by variation of the static displacement of the diaphragm due to pressure of the body against the diaphragm.

15. An acoustic-to-electrical transducer for detecting body sounds, the transducer comprising:

a diaphragm mounted in a housing such that the diaphragm can make contact with the body and vibrate in response to body sounds;

the diaphragm including means to modulate an electromagnetic signal via mechanical movement, said electromagnetic signal being an electric or magnetic field in the space behind the diaphragm or a light beam in the space behind the diaphragm;

the diaphragm being mounted such that the diaphragm can be displaced at least about or exceeding 0.1 mm due to a combination of body vibration and static pressure of the body on the diaphragm;

conversion means to convert said electromagnetic signal to an electrical signal measurement of diaphragm movement.

16. An acoustic-to-electrical transducer according to claim 15, wherein diaphragm displacement due to static pressure of the body against the diaphragm modifies the amplitude and frequency response of the electrical signal measurement of diaphragm vibration.

17. The transducer according to claim 15, further comprising:

a permanently magnetized material attached to the diaphragm such that a magnetic field behind the diaphragm is changed due to displacement of the diaphragm;

a magnetic field to electrical signal conversion means placed behind the diaphragm to convert said magnetic field changes to an electrical signal.

18. The transducer according to claim 15, further comprising:

an electrical conductor attached to the diaphragm, said conductor connected to an electrical circuit such that the conductor generates a magnetic field behind the diaphragm;

a magnetic field sensing means placed behind the diaphragm and spaced at least about or exceeding 0.1 mm from it, said magnetic field sensing means connected to an electrical circuit to convert magnetic field changes due to diaphragm movement to electrical signals.

19. The transducer according to claim 15 further comprising:

an electrical coil mounted to the diaphragm normal to the surface of the diaphragm;

a permanent magnet or electromagnet placed behind the diaphragm such that the electrical coil and magnet form a magnetic circuit such that diaphragm displacement produces changes in electrical coil current or voltage;

an electrical circuit connected to said electrical coil to convert diaphragm motion to an electrical signal.

20. The transducer according to claim 15 further comprising:

a permanent magnet or electromagnet mounted to the diaphragm normal to the surface of the diaphragm;

an electrical coil placed behind the diaphragm such that the electrical coil and magnet form a magnetic circuit such that diaphragm displacement produces changes in electrical coil current or voltage;

an electrical circuit connected to said electrical coil to convert diaphragm motion to an electrical signal.

21. The transducer according to claim 15 further comprising:

an optically reflective plane on the diaphragm; a light emitter placed behind the diaphragm emitting a beam of light aimed at said reflective plane;

a light detector positioned such that the reflected beam from the reflective plane impinges on the detector, said reflected beam being modified due to diaphragm motion;

a conversion means connected to said detector to convert diaphragm motion into an electrical signal.

22. The transducer according to claim 21 wherein the optically reflective plane has a spatial pattern such that reflection is a function of the point on the plane at which reflection occurs.

23. The transducer according to claim 15 further comprising:

an optically transmissive element mounted normal to the surface of the diaphragm that moves with diaphragm movement;

a light emitter and detector placed behind the diaphragm such the a light beam passes from emitter to detector through the movable optically transmissive element;

a conversion means connected to said detector to convert diaphragm motion into an electrical signal.

24. The transducer according to claim 23 wherein the optically transmissive element has a spatial pattern such that transmission of light is a function of the position on the element through which the beam travels.

25. An acoustic-to-electrical transducer for detecting body sounds, the transducer comprising:

a diaphragm having an electrically conductive surface, the diaphragm being mounted such that the diaphragm can make contact with the body and vibrate in response to body sounds;

a fixed conductive plate substantially parallel to the diaphragm, positioned behind the diaphragm, the conductive plate being positioned at a distance about or exceeding 0.1 mm from the diaphragm, the diaphragm conductive surface and fixed conductive plate forming two plates of a capacitor and connected in the form of an electrical capacitance to electrical circuitry;

a capacitance-to-electrical conversion means to convert diaphragm-plate capacitance changes due to body sound vibration to electrical signals;

the conductive plate and capacitance-to-electrical conversion means being combined on a semiconductor substrate to form an integrated circuit acoustic-to-electrical transducer.

* * * * *